(12) United States Patent
Davis et al.

(10) Patent No.: US 6,901,287 B2
(45) Date of Patent: May 31, 2005

(54) IMPLANTABLE THERAPY DELIVERY ELEMENT ADJUSTABLE ANCHOR

(75) Inventors: Scott J. Davis, Minneapolis, MN (US); Keith Richard Carlton, Minneapolis, MN (US); Martin Theodore Gerber, Maple Grove, MN (US); Thomas Delmar Schmelzer, Lino Lakes, MN (US); John Matthew Swoyer, Andover, MN (US); Carole Anne Tronnes, St. Paul, MN (US)

(73) Assignee: Medtronic, Inc., Minneapolis, MN (US)

( * ) Notice: Subject to any disclaimer, the term of this patent is extended or adjusted under 35 U.S.C. 154(b) by 375 days.

(21) Appl. No.: 09/843,638

(22) Filed: Apr. 26, 2001

(65) Prior Publication Data

US 2002/0111659 A1 Aug. 15, 2002

(Under 37 CFR 1.47)

Related U.S. Application Data

(60) Provisional application No. 60/267,793, filed on Feb. 9, 2001.

(51) Int. Cl.⁷ .................................................. A16N 1/05
(52) U.S. Cl. ......................... 607/2; 607/126; 600/375; 604/174
(58) Field of Search ........................ 128/898, DIG. 40; 607/2, 115–117, 126, 129, 130, 131, 132; 600/372–375, 377; 604/174–175; 606/151, 157, 158

(56) References Cited

U.S. PATENT DOCUMENTS

| | | |
|---|---|---|
| 3,821,957 A | 7/1974 | Riely et al. |
| 3,827,438 A | 8/1974 | Kees, Jr. |
| 4,249,529 A | 2/1981 | Nestor et al. |
| 4,437,475 A | 3/1984 | White |
| 4,658,822 A | 4/1987 | Kees, Jr. |
| 4,672,979 A | 6/1987 | Pohndorf |

(Continued)

FOREIGN PATENT DOCUMENTS

| | | |
|---|---|---|
| EP | 0588470 A1 | 3/1994 |
| EP | 1048320 A2 | 11/2000 |

Primary Examiner—Kennedy Schaetzle
Assistant Examiner—Kristen Mullen
(74) Attorney, Agent, or Firm—Keith M. Campbell; Medtronic, Inc.

(57) ABSTRACT

An implantable therapy delivery system has a therapy delivery element that is inserted or implanted into a human body and anchored or fixed to tissue to delivery a therapy to a patient. In one embodiment an implantable neurostimulator uses an electrical stimulation lead to delivery a therapy such as sacral nerve stimulation, peripheral nerve stimulation, and the like. In another embodiment the implantable therapeutic substance delivery device, also known as a drug pump, is connected to a catheter to deliver a therapy to treat conditions such as spasticity, cancer, pain, and the like. The therapy delivery element is anchored to tissue using an adjustable anchor having a therapy grip element, at least two extension elements connected to the therapy grip element, and a tissue fixation element connected to the extension elements. The extensions project substantially perpendicular in relation to the therapy delivery element and are configured to actuate the therapy grip element to an opened position and a closed position. A tissue fixation element is connected to the extensions and configured for fixation to a tissue location from an axial direction to the therapy delivery element. The adjustable anchor facilitates minimally invasive procedures, facilitates securing the therapy delivery element in the same plane as the therapy delivery element was inserted, facilitates rapid placement to reduce procedure time, and provides a wide range of other benefits. The adjustable anchor and its methods of operation have many embodiments.

39 Claims, 11 Drawing Sheets

U.S. PATENT DOCUMENTS

| | | | |
|---|---|---|---|
| 5,036,862 A | 8/1991 | Pohndorf | |
| 5,107,856 A | 4/1992 | Kristiansen et al. | |
| 5,129,405 A | 7/1992 | Milijasevic et al. | |
| 5,152,298 A | 10/1992 | Kreyenhagen et al. | |
| 5,238,007 A | 8/1993 | Giele et al. | |
| 5,242,431 A | 9/1993 | Kristiansen | |
| 5,273,053 A | 12/1993 | Pohndorf | |
| 5,344,439 A | 9/1994 | Otten | |
| 5,395,344 A | 3/1995 | Beisang, III et al. | |
| 5,423,763 A | 6/1995 | Helland et al. | |
| 5,476,493 A | 12/1995 | Muff | |
| 5,484,445 A | 1/1996 | Knuth | |
| 5,584,874 A | 12/1996 | Rugland et al. | |
| 5,603,730 A * | 2/1997 | Romkee | 607/116 |
| 5,628,780 A | 5/1997 | Helland et al. | |
| 5,632,729 A | 5/1997 | Cai et al. | |
| 5,683,446 A | 11/1997 | Gates | |
| 5,735,891 A | 4/1998 | White | |
| 5,746,722 A | 5/1998 | Pohndorf et al. | |
| 5,792,112 A | 8/1998 | Hart et al. | |
| 5,824,032 A | 10/1998 | Belden | |
| 5,843,146 A | 12/1998 | Cross, Jr. | |
| 5,931,861 A * | 8/1999 | Werner et al. | 607/115 |
| 5,938,596 A * | 8/1999 | Woloszko et al. | 600/377 |
| 5,957,968 A | 9/1999 | Belden et al. | |
| 6,055,456 A | 4/2000 | Gerber | |
| 6,134,477 A | 10/2000 | Knuteson | |

\* cited by examiner

IMPLANTABLE THERAPY DELIVERY ELEMENT ADJUSTABLE ANCHOR

CROSS-REFERENCE TO RELATED APPLICATIONS

This application claims priority to U.S. Provisional Application Ser. No. 60/267,793, filed on Feb. 9, 2001.

BACKGROUND OF THE INVENTION

This disclosure relates to a medical device and more particularly to an implantable stimulation lead anchor for fastening a therapy delivery element such as a stimulation lead or catheter to a human body.

The medical device industry produces a wide variety of electronic and mechanical devices for treating medical conditions. Depending upon the medical condition, medical devices can be surgically implanted or connected externally to the patient receiving treatment. Clinicians use medical devices alone or in combination with therapeutic substance therapies and surgery to treat medical conditions. For some medical conditions, medical devices provide the best, and sometimes the only, therapy to restore an individual to a more healthful condition and a fuller life. One type of medical device is an implantable neurostimulator.

A neurostimulator such as an InterStim® Model 3023 available from Medtronic, Inc. in Minneapolis, Minn. can be used to treat conditions such as pain and pelvic floor disorders. The neurostimulator is typically connected to a stimulation lead to deliver electrical stimulation to a specific location in the patient's body. When the stimulation lead is inserted or implanted, it is typically anchored using a lead anchor to fix the stimulation lead to tissue. The lead anchor is important for the insertion or implantation procedure because the lead anchor is intended to prevent the stimulation lead from migrating away from a specifically selected stimulation site. In order to reduce lead migration, it is often desirable to anchor the stimulation lead in the same plane that the stimulation lead was inserted. The anchor is often used during surgical procedures where there is limited space to insert the anchor, limited space to operate the anchor, limited space to secure the anchor to tissue, and time constraints to complete the procedure rapidly. For some procedures, installing the anchor can be one of the most time consuming and invasive portions of the stimulation lead insertion procedure. Clinicians inserting and anchoring therapy delivery elements typically prefer to perform the procedure rapidly, in a minimally invasive manner, and fix the therapy delivery element in a manner that reduces the opportunity for the therapy delivery element to migrate if practicable. Previous stimulation lead anchors can have one or more of the following limitations along with other limitations such as being difficult to use for minimally invasive procedures, difficult to secure the simulation lead in the same plane as the stimulation lead was inserted, and inconvenient actuation from an open position to a closed position, and the like. Examples of some previous stimulation lead anchors are shown in U.S. Pat. No. 6,134,477 "Adjustable Medical Lead Fixation System" by Knuteson (Oct. 17, 2000); U.S. Pat. No. 5,484,445 "Sacral Lead Anchoring System" by Knuth (Jan. 16, 1996); and, U.S. Pat. No. 5,843,146 "Adjustable Medical Lead Anchor" by Cross, Jr. (Dec. 1, 1998).

For the foregoing reasons, there is a need for a therapy delivery element anchor that facilitates minimally invasive procedures, facilitates securing the therapy delivery element in the same plane as the therapy delivery element was inserted, facilitates rapid placement to reduce procedure time, and has many other improvements.

SUMMARY OF THE INVENTION

The implantable therapy delivery system having an adjustable anchor has a tissue fixation element configured for fixation to a tissue location from an axial direction to the therapy delivery element. The tissue fixation element is connected to at least two extension elements that extend substantially perpendicular from the therapy delivery element. The extension elements are connected to a therapy grip element, and the extension elements are configured to actuate the therapy grip element to an open position to disengage from the therapy delivery element and a closed position to engage the therapy delivery element. The adjustable anchor is coupleable to therapy delivery elements such as neurostimulation electrical leads and therapeutic substance infusion catheters. The therapeutic delivery element is coupleable to an implantable therapy delivery device such as a neurostimulator or a therapeutic substance delivery device. The adjustable anchor facilitates minimally invasive procedures, facilitates securing the therapy delivery element in the same plane as the therapy delivery element was inserted, facilitates rapid placement to reduce procedure time, and provides a wide range of other benefits. The adjustable anchor and its methods of operation have many embodiments.

DETAILED DESCRIPTION OF THE PREFERRED EMBODIMENTS

Figure 1A:
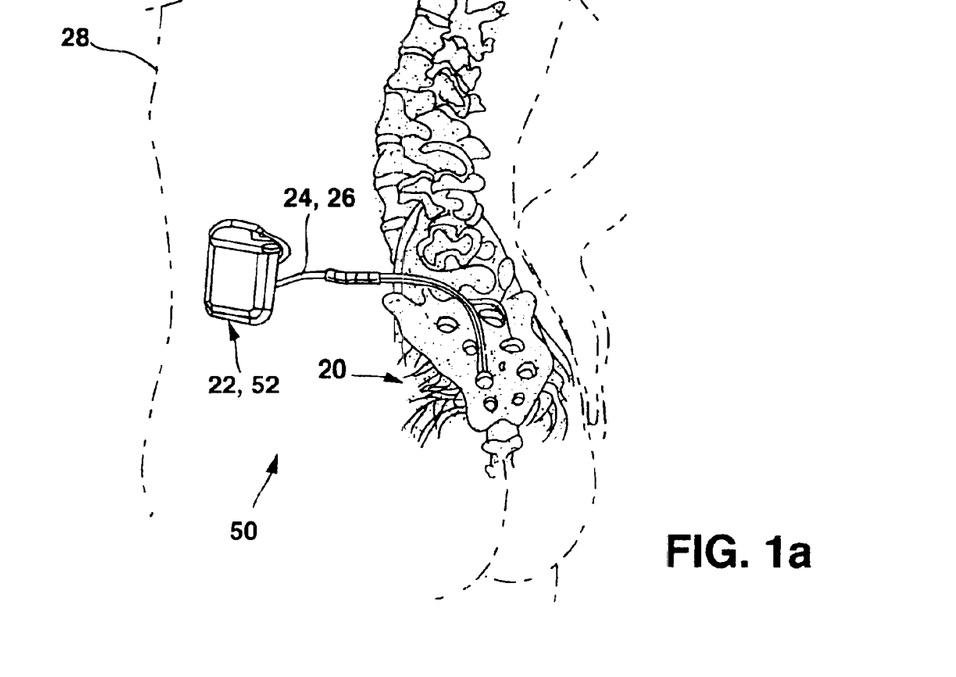
FIGS. 1a–1b show general environmental view for an adjustable anchor embodiment.
Figure 1B:
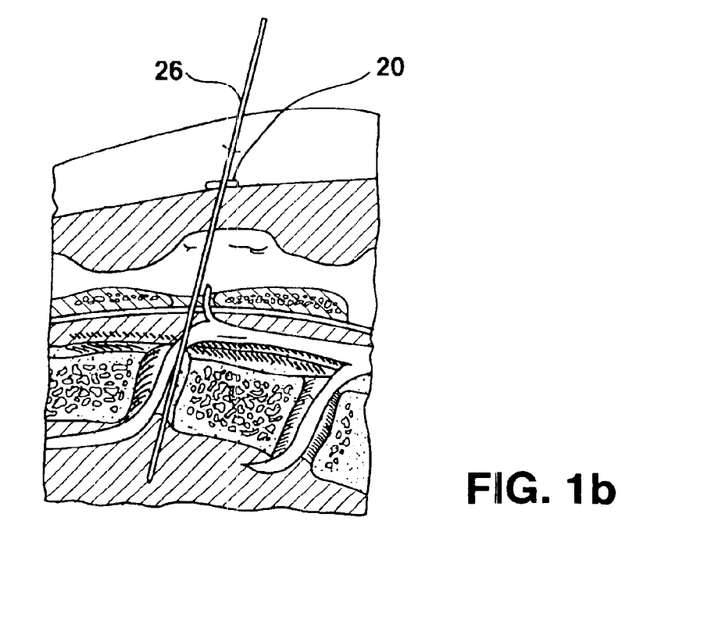

FIGS. 1a–1b show a general environmental view for an adjustable anchor 20 embodiment used for sacral nerve stimulation. Sacral nerve stimulation is performed to treat pelvic floor disorders such as urinary control disorders, fecal control disorders, sexual dysfunction, pelvic pain, and the like. The therapy delivery device 52 is a neurostimulator 22 such as an InterStim® Model 3023 available from Medtronic, Inc. in Minneapolis, Minn. and the therapy delivery element 24 is a stimulation lead 26. The neurostimulator 22 is typically implanted subcutaneously in the patient's body 28 at a location selected by the clinician. The stimulation lead 26 is typically fixed in place near the location selected by the clinician using a device such as the adjustable anchor 20. The adjustable anchor 20 can be positioned on the stimulation lead 26 in a wide variety of locations and orientations to accommodate individual anatomical difference and the preferences of the clinician. After the stimulation lead 26 is anchored, also known as fixed, the stimulation lead 26 can be connected to the neurostimulator 22. If the clinician desires to operate in a minimally invasive manner, the adjustable anchor 20 can be secured to the stimulation lead 26, implanted, and fixed to tissue either through a dilator tube or through a small incision.

The adjustable anchor 20 is positioned on the therapy delivery element 24 and then fixed to the patient's body 28 to prevent or reduce therapy delivery element 24 migration. The adjustable anchor 20 is fixed to tissue with a mechanical attachment such as a suture, a staple, a bone screw, and the like. The tissue selected for fixing the adjustable anchor 20 is typically tissue such as a subcutaneous fascia layer, bone, and the like. Although a specific neurostimulation environment is shown many other environments for the adjustable anchor 20 are possible such as other neurostimulation environments and therapeutic substance delivery device, also known as a drug pump with catheter, environments.

Figure 2A:
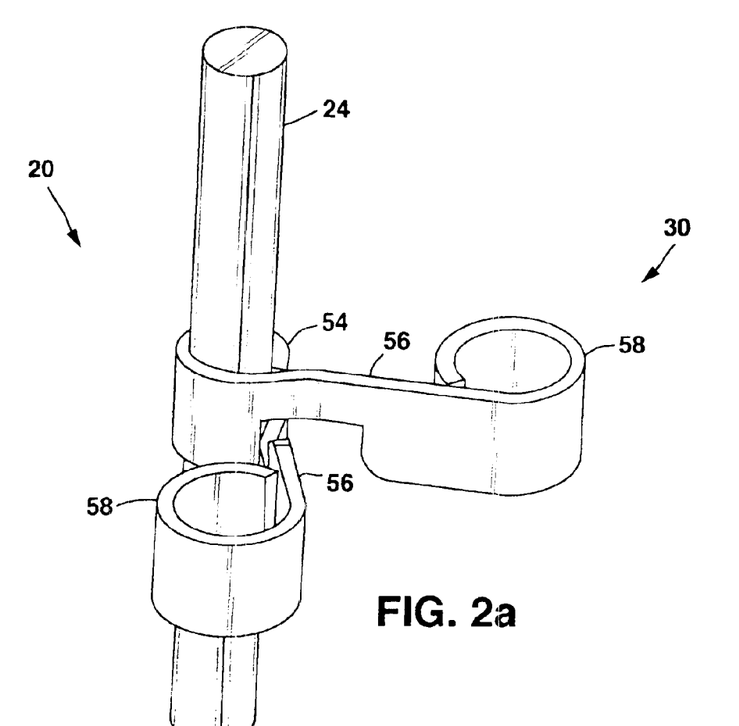
FIGS. 2a–2b show views of a first embodiment of the adjustable anchor.
Figure 9A:
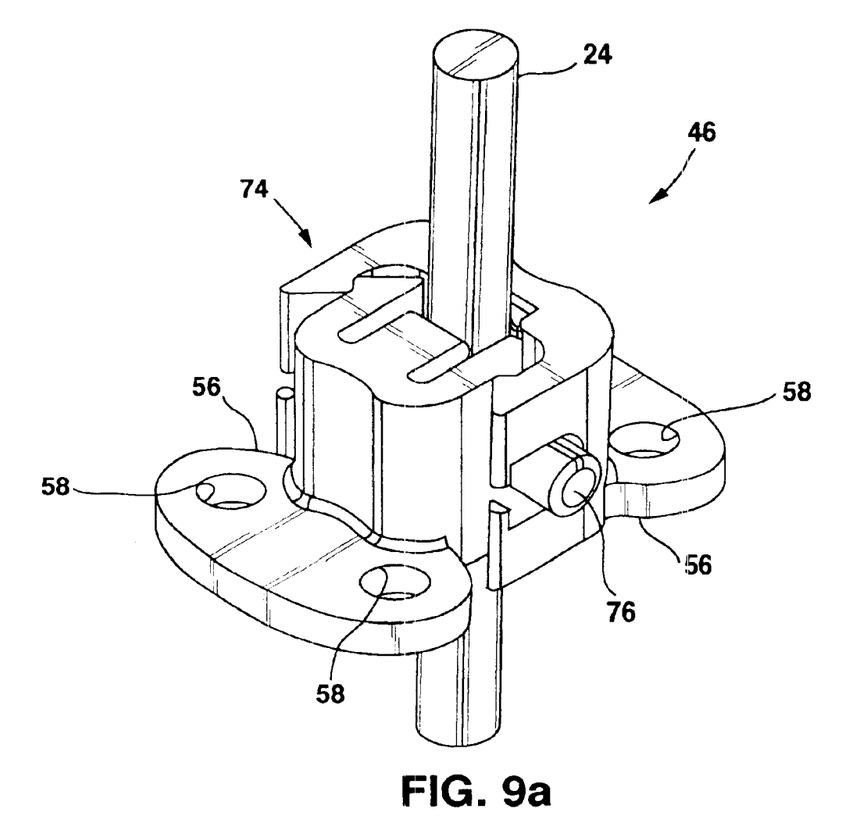
FIGS. 9a–9b show views of a ninth embodiment of the adjustable anchor.
Figure 9B:
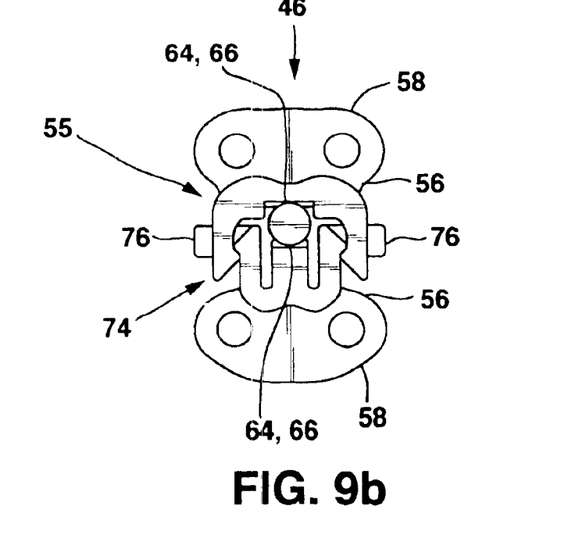
Figure 10A:
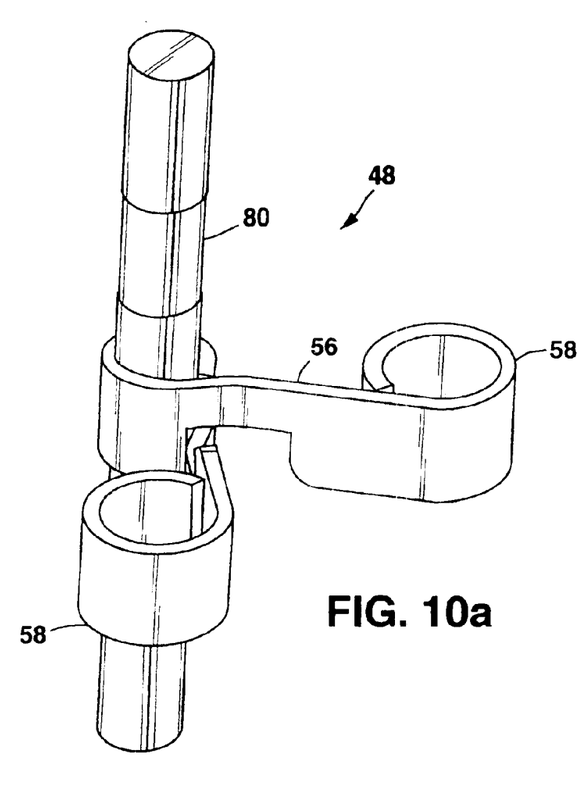
FIGS. 10a–10b show views of a tenth anchor position reference embodiment.
Figure 10B:
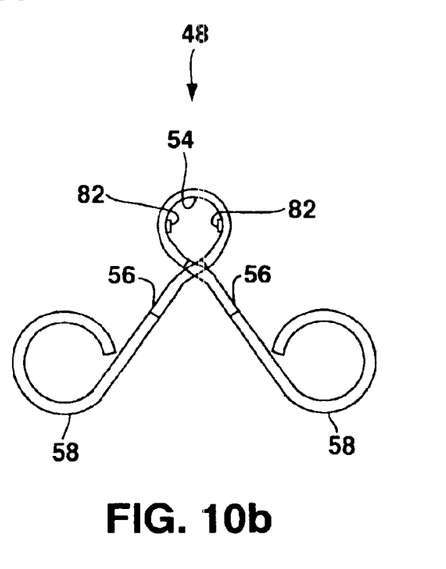

FIGS. 2a–10b show various embodiments of the adjustable anchor 20. More specifically, FIGS. 2a–2b show a first embodiment 30; FIG. 2c shows a second embodiment 32; FIGS. 3a–3d show a third embodiment 34; FIGS. 4a–4b show a forth embodiment 36; FIGS. 5a–5d show a fifth embodiment 38; FIGS. 6a–6d show a sixth embodiment 40; FIGS. 7a–7d show a seventh embodiment 42; FIGS. 8a–8d show an eighth embodiment 44; FIGS. 9a–9b show a ninth embodiment 46; and FIGS. 10a–10b show a tenth embodiment 48. An implantable therapy delivery system 50 having an adjustable anchor 20 comprises an implantable therapy delivery device 52, at least one therapy delivery element 24, and an adjustable anchor 20. The implantable therapy delivery device 52 can be a neurostimulator 22, a diagnostic recorder, or a therapeutic substance delivery device, also known as a drug pump, and the like. The therapy delivery element 24 can be an electrical lead such as a stimulation lead 26 or a sensing lead, or a catheter. The stimulation lead 26 can be a Medtronic Model 3886 quadrapolar lead having a diameter of approximately 0.127 cm (0.050 inch). When the implantable therapy delivery device 52 is a neurostimulator 22 with a stimulation lead 26, therapies can be performed such as sacral nerve stimulation, peripheral nerve stimulation, spinal cord stimulation, and the like. When the implantable therapy delivery device 52 is a therapeutic substance delivery device with a catheter, therapies can be performed to treat conditions such as spasticity, pain, cancer, and the like.

The adjustable anchor 20 is coupleable to the therapy delivery element 24 and includes a therapy grip element 54, at least two extension elements 56, and a tissue fixation element 58. The adjustable anchor 20 is implantable in a patient's body 28 but can also be used external to the body 28 to anchor an inserted therapy delivery element 24 that extends outside the body 28. The adjustable anchor 20 is manufactured from materials that are biocompatible such as a rigid plastic, polysulfone, titanium, surgical steel, shape memory metal (Nitinol), silicone, and the like.

The therapy grip element 54 is configured for actuation to an open position 60 and a closed position 62. The therapy grip element 54 serves as a means for gripping the therapy delivery element 24 to selectively open 60 to disengage and close 62 to engage the therapy delivery element 24. The therapy grip element 54 can be configured with a variety of grip surfaces 55 that function to secure the therapy delivery element 24 while not damaging the therapy delivery element 24 such as a substantially rigid grip surface, an elastic grip surface with a material such as a shape memory metal (FIGS. 8b–8d), and the like. The therapy grip element 54 can be configured with at least two friction pads 64 that engage the therapy delivery element 24 at substantially opposing angles. The therapy grip element ends 66 can be radiused to reduce strain that the therapy grip element 54 can produce on the therapy delivery element 24. The therapy grip element 54 can create stress on the therapy delivery element 24 when the adjustable anchor 20 is secured in the patient 28 and during movement of the therapy delivery element 24 after implantation.

For embodiments where the therapy delivery element 24 is a stimulation lead 26, the therapy grip element 54 is configured to grip the stimulation lead 26 in a manner that does not damage or constrict the internal stimulation conductor. The therapy grip element 54 can be configured to avoid compressing the outer surface of the stimulation lead 26 by more than about 20% to reduce the risk that the internal stimulation conductor will become damaged. When the therapy grip element 54 is open 60, the therapy grip element 54 clears the therapy delivery element 24 by a sufficient distance to permit a clinician to place the therapy grip element 54 at a desired location on the therapy delivery element 24 such as with a clearance of at least about 0.0025 cm (0.001 inch). For embodiments where the therapy delivery element 24 is an implantable catheter, the therapy grip element 54 is configured to grip the catheter in a manner that does not damage or constrict the catheter lumen in a manner that unduly restricts delivery of a therapeutic substance. The therapy grip element 54 can be configured to avoid compressing the outer surface of the catheter by more than about 20% to reduce the risk that the catheter will become damaged or restrict delivery of a therapeutic substance.

Figure 2B:
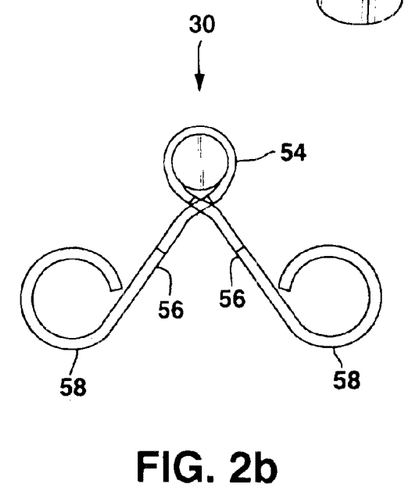
Figure 2C:
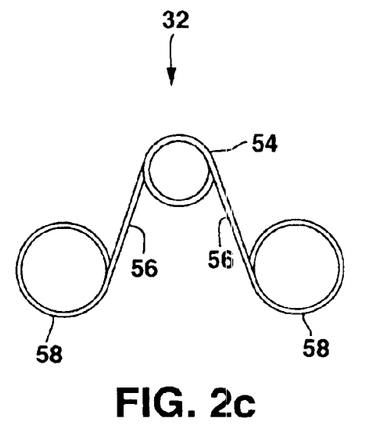
FIG. 2c shows a second embodiment of the adjustable anchor.
Figure 3A:
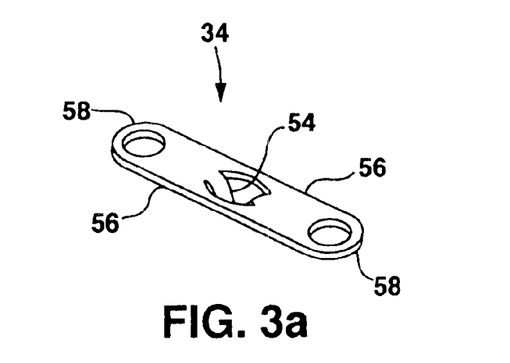
FIGS. 3a–3d show views of a third embodiment of the adjustable anchor.
Figure 3B:
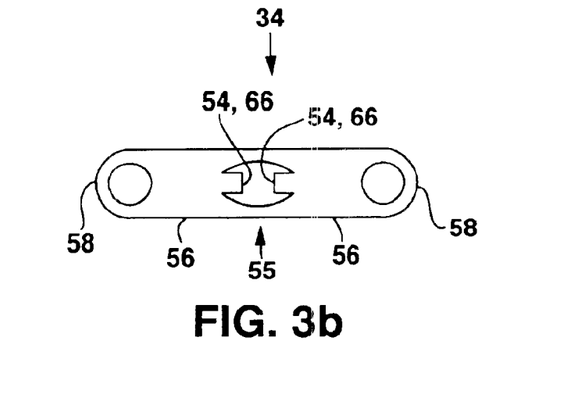
Figure 3C:
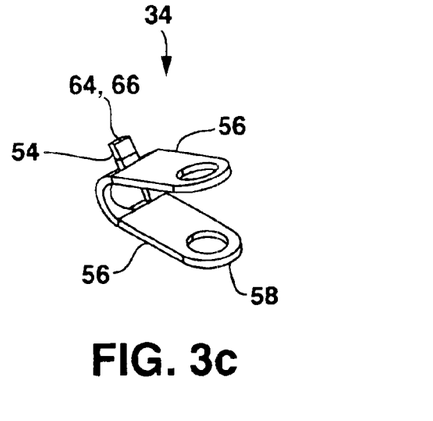
Figure 3D:
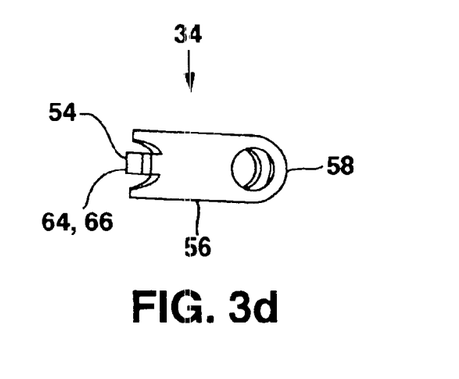
Figure 4A:
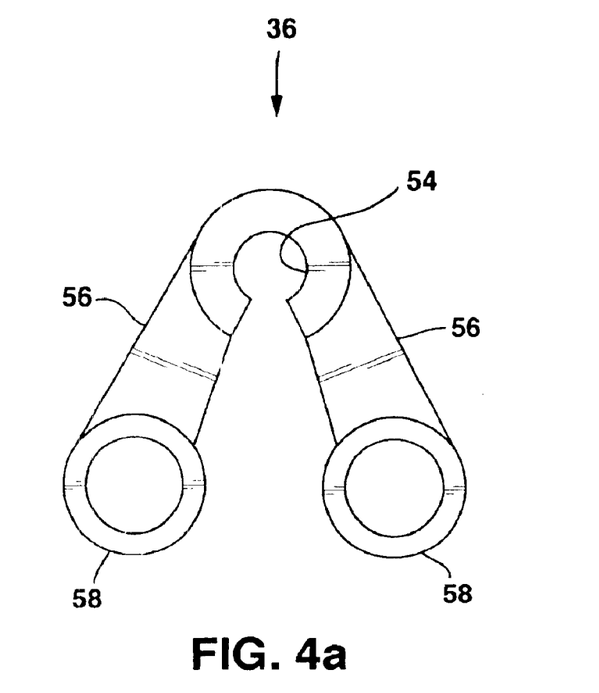
FIGS. 4a–4b show views of a forth embodiment of the adjustable anchor.
Figure 4B:
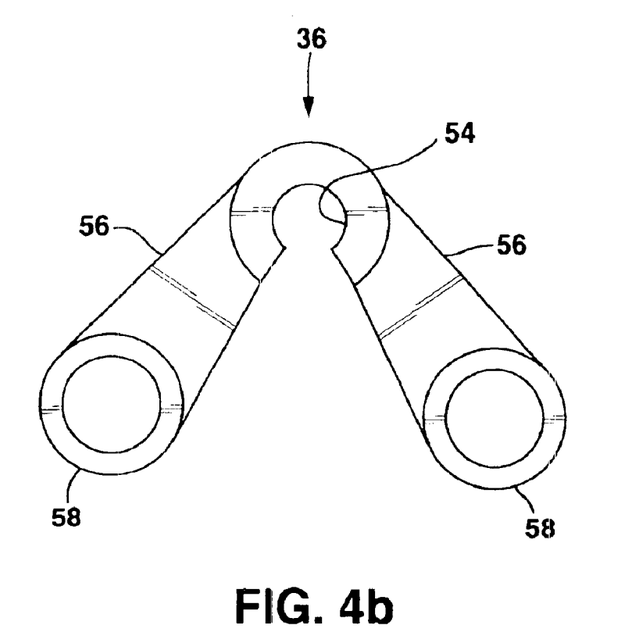
Figure 5A:
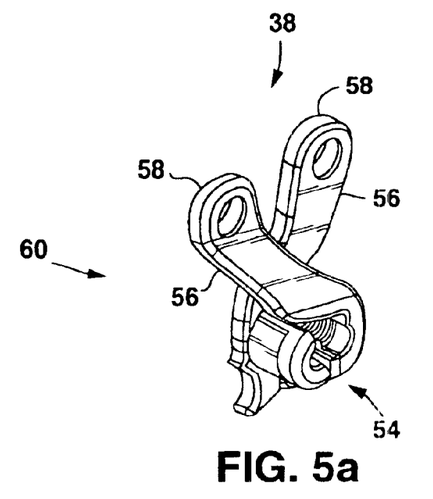
FIGS. 5a–5d show views of a fifth embodiment of the adjustable anchor.
Figure 5B:
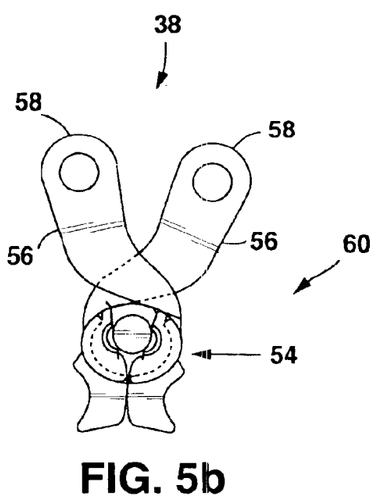
Figure 5C:
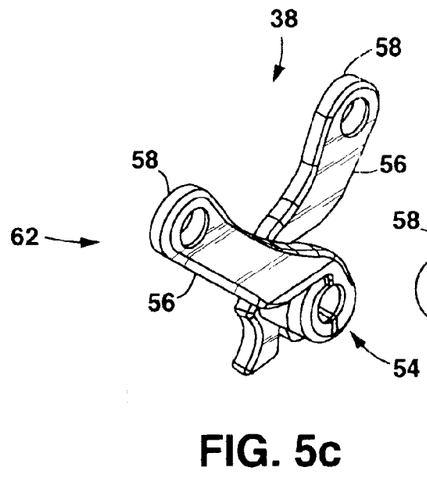
Figure 5D:
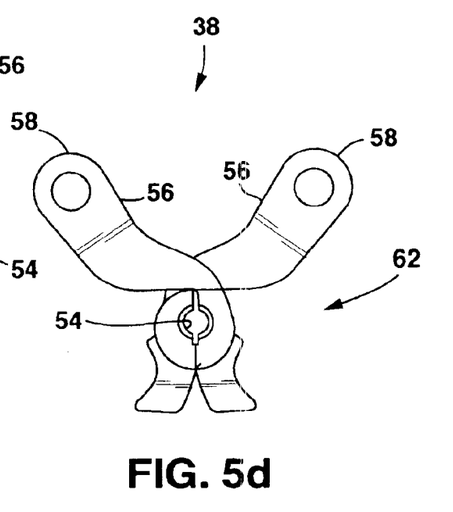
Figure 6A:
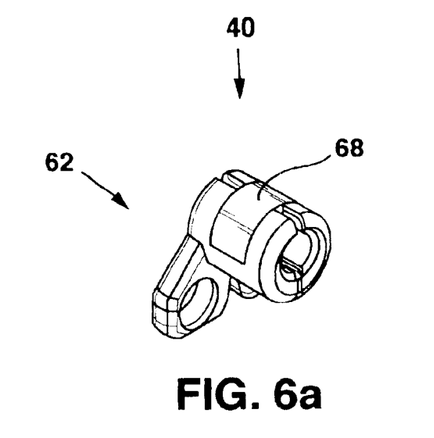
FIGS. 6a–6d show views of a sixth embodiment of the adjustable anchor.
Figure 6B:
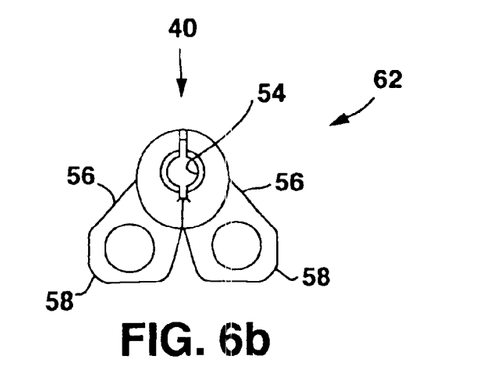
Figure 6C:
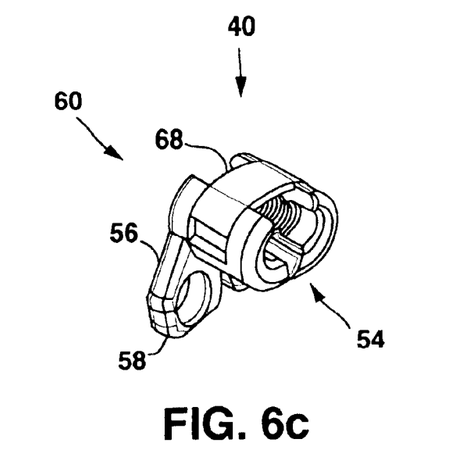
Figure 6D:
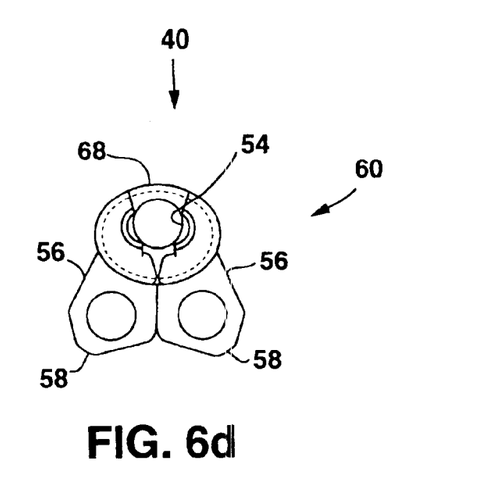
Figure 7A:
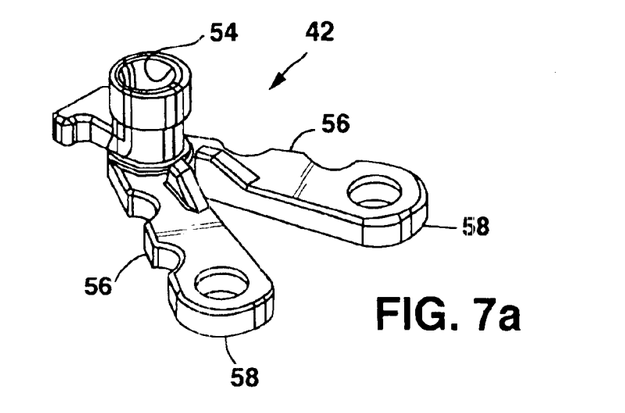
FIGS. 7a–7d show views of a seventh embodiment of the adjustable anchor.
Figure 7B:
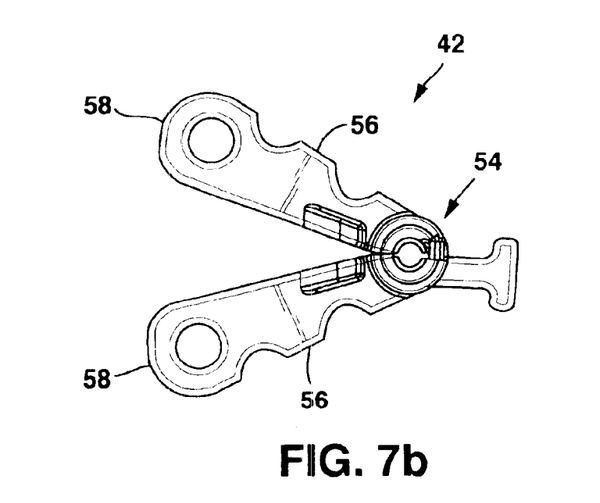
Figure 7C:
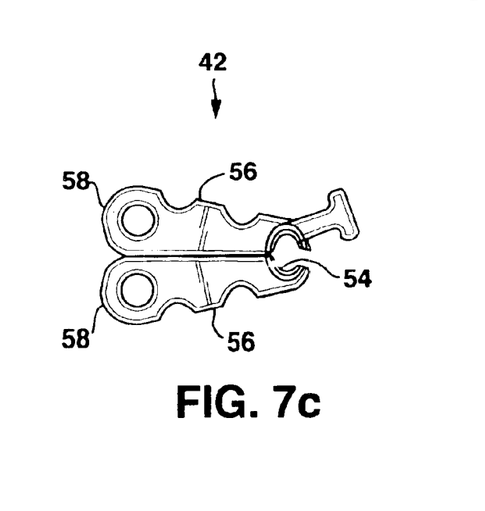
Figure 7D:
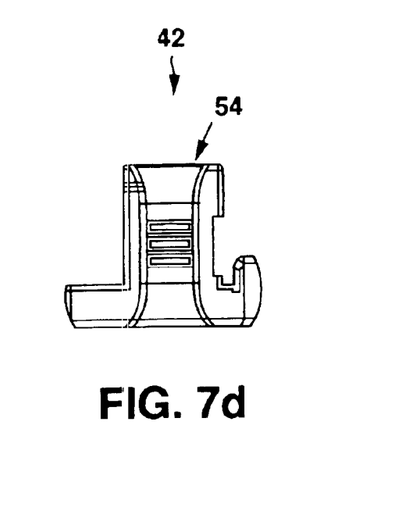
Figure 8A:
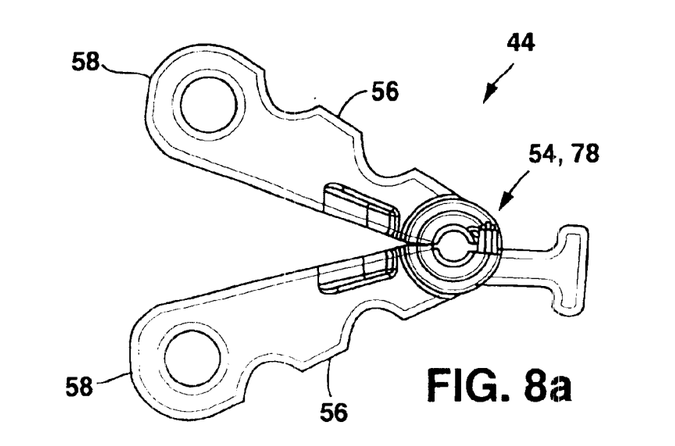
FIGS. 8a–8d show views of an eighth embodiment of the adjustable anchor.
Figure 8B:
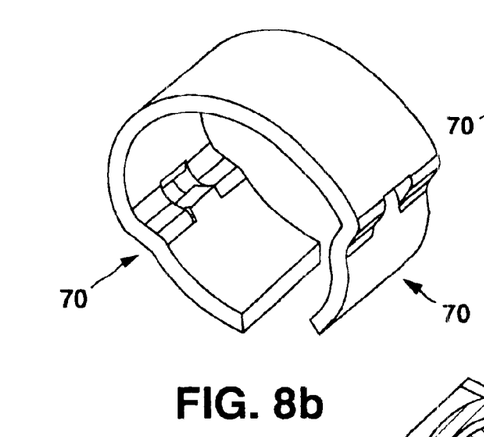
Figure 8C:
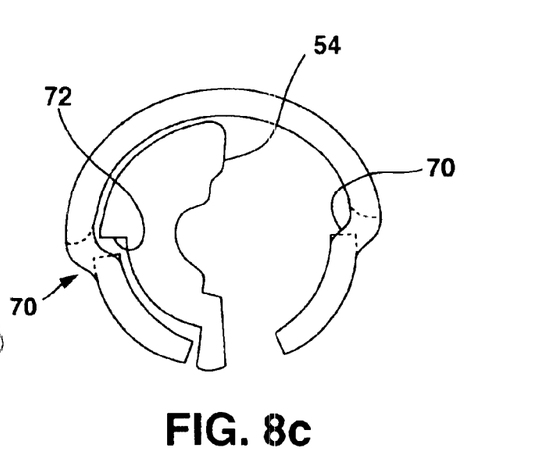
Figure 8D:
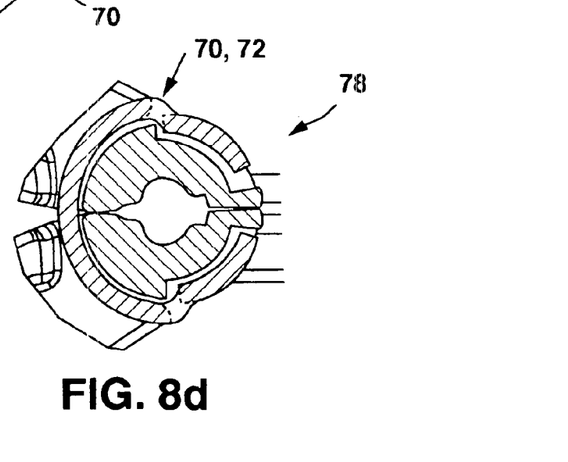

The therapy grip element 54 can be configured in a normally closed position 62 or a normally open position 60. When configured in the normally closed position 62, the risk of unintended opening of the therapy grip element 54 is reduced. For the normally closed embodiment, the therapy grip element 54 can include a biasing element 68 (FIG. 6a) such as a shape memory metal to bias the therapy grip element 54 in a closed position 62. Some embodiments of the therapy grip element 54 (FIGS. 8a–8d) can include a grip stop surface 70 that engages a complimentary extension stop surface 72 to prevent the extension element 56 from actuating the therapy grip element 54 beyond a desired actuation limit. The therapy grip element 54 can wrap around the therapy delivery element 24 in the range from at least about 25 degrees (FIGS. 3b and 9b) to at least about 270 degrees (FIGS. 2b and 4a). In some embodiments such as shown in FIG. 2c, the therapy grip element 54 can wrap around the therapy delivery element 24 more than about 360 degrees (FIG. 2c) of the therapy delivery element 24. In embodiments where the therapy grip element 54 wraps around the therapy delivery element 24 by more than about 180 degrees (FIG. 7c), the therapy grip element 54 is typically placed over an end of the therapy delivery element 24 to position the therapy grip element 54 on the therapy delivery element 24. In embodiments where the therapy grip element 54 in the open position 60 wraps around the therapy delivery element 24 by less than about 180 degrees, the therapy grip element 54 can be placed either over the end of the therapy delivery element 24 or inserted along the length of the therapy delivery element 24. When this embodiment is placed in the closed position 62, the fixation element 58 can either completely encircle the therapy delivery element 24 or only partially encircle the therapy delivery element 24 such as in the range from about 20 degrees to less than about 360 degrees.

FIGS. 9a–9b shows a therapy grip element 54 that uses opposing grip surfaces 55. Each opposing grip surface 55 is carried on a separate therapy grip element 54 component. The therapy grip element 54 is closed by mating the separate therapy grip elements 54 together. As the separate therapy grip element 54 components are mated together, the complementary ramped surfaces 74 on both components engage and then lock into position. The therapy grip element 54 is opened by the release tabs 76 to unlock the therapy grip element 54 by disengaging the ramped surfaces 74, so the therapy grip element 54 can be actuated from a closed position 62 to an open position 60.

The extension elements 56 are connected to the therapy grip element 54 and extend substantially perpendicular from the therapy delivery element 24. The extension elements 56 are configured to actuate the therapy grip element 54. The two extension elements 56 can be actuated with a single pincer motion. The extension elements 56 serve as a means for extension and extend from the means for gripping 54 substantially perpendicular to the therapy delivery element 24 to selectively actuate the means for gripping 54 to engage and disengage the therapy delivery element 24. The extension elements 56 can be positioned so the angle between the extension elements 56 and the therapy delivery element 24 is about 180 degrees or less than about 180 degrees. In the open position 60, these extension elements 56 are typically in the range from about 60 degrees to about 120 degrees. The extension elements 56 are size to provide an adequate lever arm to actuate the therapy grip element 54 and to position the tissue fixation element 58. In some embodiments, the extension elements 56 are positioned at less than 180 degrees in relation to each other so the extension elements 56 can be more easily actuated with a tool such as forceps or one hand of the clinician. In some embodiments, the extension elements 56 can include a grip stop 78 (FIGS. 8a–8d) to prevent over actuation of the therapy grip element 54. The extension elements 56 can be configured with various profiles to facilitate the use of an actuation tool such as forceps and to accommodate patient anatomical features.

The tissue fixation element 58 is connected to the extension elements 56 and is configured for fixation to a tissue location from an axial direction to the therapy delivery element 24 (FIG. 9). The tissue fixation element 58 serves as a means for tissue fixation 58 for fixing the means for extension 56 to a tissue location from an axial direction to the therapy delivery element 24. The tissue location can be near where the therapy delivery element 24 enters the patient's body 28 on subcutaneous tissue. The tissue fixation element 58 can be configured to accept tissue fixation techniques such as a suturing, stapling, and screwing. The tissue fixation element 58 is configured at a predetermined position in relation to the extension element 56. For example, the extension elements 56 can be configured to position the tissue fixation element 58 away from the foramen. In some embodiments, when the therapy grip element 54 is closed 62, the extension elements 56 overlap and the tissue fixation elements 58 overlap to permit fixation to tissue with a single suture, staple, screw, and the like.

FIGS. 10a–10b show an anchor position reference fifth embodiment 48. In some embodiments, the therapy delivery element 24 has at least one therapy position reference 80. The therapy position reference 80 is any reference that provides the clinician with feedback on the position of the adjustable anchor 20 such as a visual reference, a tactile reference, an indentation, a protrusion, and the like. The therapy position reference 80 is set at a predetermined location such as a certain distance from electrical contacts used for stimulation. In some embodiments, the therapy grip element 54 can include an anchor position reference 82. The anchor position reference 82 is typically complimentary to the therapy position reference 80 such as an indentation, a protrusion, and the like. The anchor position reference 82 engages the therapy position reference 80 to provide the clinician with feedback on the position of the adjustable anchor 20 on the therapy delivery element 24.

The various embodiments of the adjustable anchor 20 disclosed in FIGS. 2a–10b each provide different features that a clinician can select based upon considerations such as the procedure, patient, and therapy delivery element. For example, the second embodiment 32 can be selected when minimizing adjustable anchor 20 residential space is desired.

Operation

Figure 11:
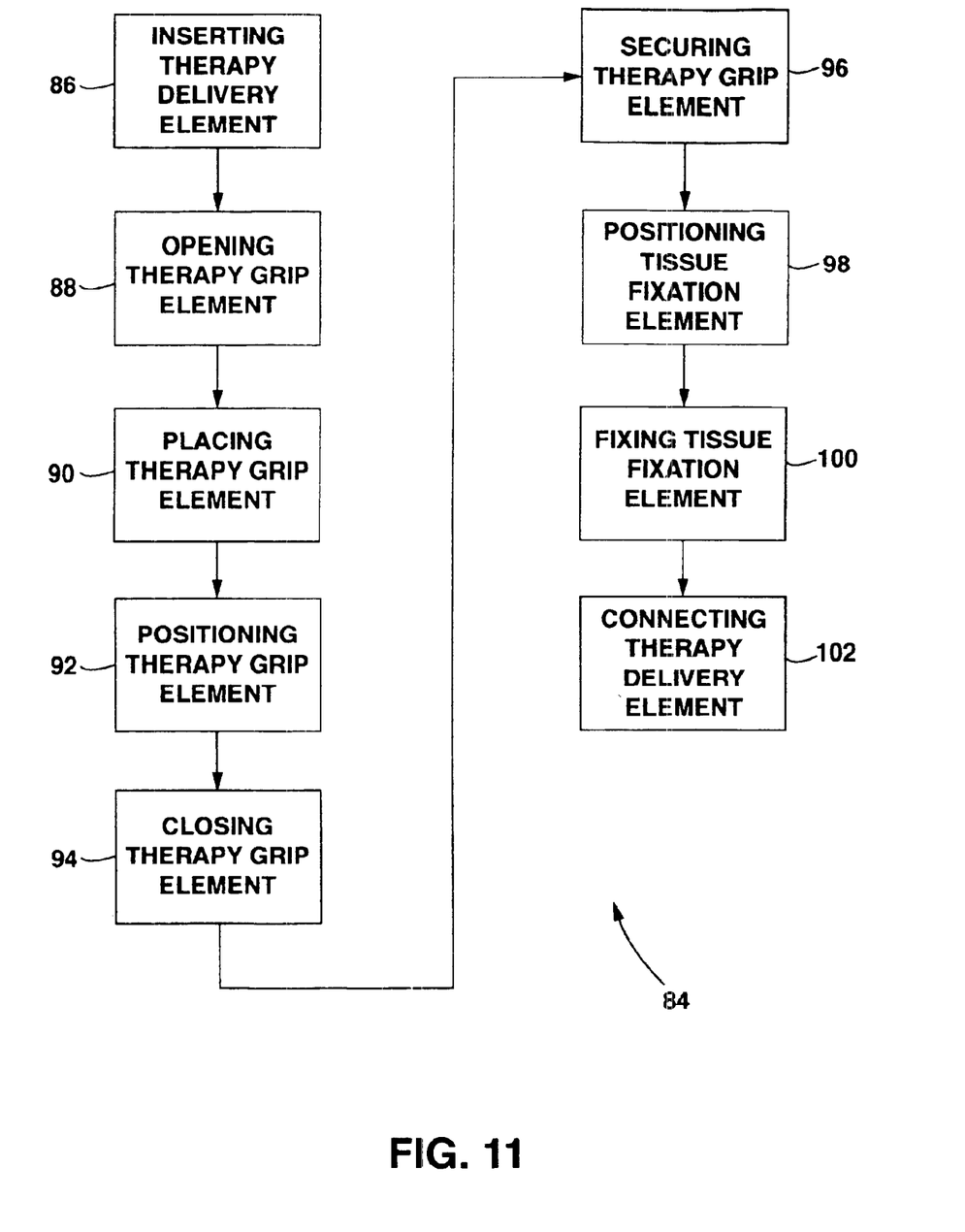
FIG. 11 shows a flow diagram of a method for operating an adjustable anchor embodiment.

FIG. 11 shows a flow diagram of a method for operating an adjustable anchor embodiment 84, and FIG. 2a shows an adjustable anchor 20. The method for anchoring a therapy delivery element 84 permits a clinician to accurately locate the adjustable anchor 20 close to the where therapy is being delivered to reduce the opportunity for therapy delivery element 24 migration, and the method permits the clinician to rapidly use the adjustable anchor 20 with minimally invasive procedures. The method 84 begins by inserting 86 a therapy delivery element 24 into a patient's body 28. The therapy grip element 54 is opened 88 by actuating two extension elements 56. The extension elements 56 can be actuated with a single pincer motion to facilitate rapid actuation of the therapy grip element 54. The therapy grip element 54 is placed 90 on the therapy delivery element 24. The therapy grip element 54 is positioned 92 at a grip location on the therapy delivery element 24. The therapy grip element 54 is closed 94 on the therapy delivery element 24 by actuating the two extension elements 56. When the therapy grip element 54 is closed 94, the therapy grip element 54 is secured 96 on the therapy delivery element 24. The tissue fixation element 58 is positioned 98 at a tissue location. The tissue location is typically near where the therapy delivery element 24 enters the patient's body 28 on subcutaneous tissue. The tissue fixation element 58 is fixed 100 at the tissue location typically in an orientation along the axial length of the therapy delivery element 24. The therapy delivery element 24 such as a stimulation lead 26 or catheter is connected 102 to the therapy delivery device 52. The therapy delivery device 52 can be a neurostimulator 22 or a therapeutic substance delivery device.

Embodiments having an anchor position reference 82 to assist a clinician in positioning the adjustable anchor 20 on the therapy delivery element 24 can include the following elements. The adjustable anchor's grip location is sensed on the therapy delivery element 24. The grip location can be sensed with using an anchor position reference 82 that can be a visual reference, a tactile reference, an indentation, a protrusion, and the like.

Thus, embodiments of the implantable therapy delivery element adjustable anchor 20 and its method of operation are disclosed to facilitate minimally invasive procedures, facilitate securing the therapy delivery element 24 in the same plane as the therapy delivery element 24 was inserted, facilitate rapid placement to reduce procedure time, and provide many other improvements. One skilled in the art will appreciate that the present invention can be practiced with embodiments other than those disclosed. The disclosed embodiments are presented for purposes of illustration and not limitation, and the present invention is limited only by the claims that follow.

What is claimed is:

1. A method for operating an adjustable anchor for a therapy delivery element, comprising:

providing a therapy grip element having a length defined by the boundaries of a first and second opening;

separating a first portion of the therapy grip element from a second portion of the therapy grip element to form a discontinuous inner surface extending the length of the therapy grip element by actuating two extension elements to open the therapy grip element;

placing the therapy element within the inner surface of the therapy grip element;

positioning the therapy grip element at a grip location on the therapy delivery element;

closing the therapy grip element on the therapy delivery element by actuating the two extension elements such that the inner surface of the grip element grippably engages the therapy delivery element;

securing the therapy grip element on the therapy delivery element when the therapy grip element is closed;

positioning a tissue fixation element at a tissue location;

fixing the tissue fixation element to tissue at the tissue location in an orientation along the axial length of the therapy delivery element.

2. The method as in claim 1 further comprising sensing therapy grip element location on the therapy delivery element while positioning the therapy grip element at the grip location on the therapy delivery element.

3. The method as in claim 1 wherein the tissue location is near where the therapy delivery element enters the human body on subcutaneous tissue.

4. The method as in claim 1 wherein the two extension elements are actuated with a single pincer motion.

5. A method for anchoring a therapy delivery element, comprising:

inserting a therapy delivery element into a human body;

providing a therapy grip element having a length defined by the boundaries of a first and second opening;

separating a first portion of the therapy grip element from a second portion of the therapy grip element to form a discontinuous inner surface extending the length of the therapy grip element by actuating two extension elements to open the therapy grip element;

placing the therapy element within the inner surface of the therapy grip element;

positioning the therapy grip element at a grip location on the therapy delivery element;

closing the therapy grip element on the therapy delivery element by actuating the two extension elements such that the inner surface of the grip element grippably engages the therapy delivery element;

securing the therapy grip element on the therapy delivery element when the therapy grip element is closed;

positioning a tissue fixation element at a tissue location;

fixing the tissue fixation element to tissue at the tissue location in an orientation along the axial length of the therapy delivery element; and, connecting the therapy delivery element to a therapy delivery device.

6. The method as in claim 5 further comprising sensing therapy grip element location on the therapy delivery element while positioning the therapy grip element at the grip location on the therapy delivery element.

7. The method as in claim 5 wherein the tissue location is near where the therapy delivery element enters the human body on subcutaneous tissue.

8. The method as in claim 5 wherein the two extension elements are actuated with a single pincer motion.

9. The method as in claim 5 wherein the therapy delivery device is a neurostimulator.

10. The method as in claim 5 wherein the therapy delivery device is a therapeutic substance delivery device.

11. The method as in claim 5 wherein the therapy delivery element is a stimulation lead.

12. The method as in claim 5 wherein the therapy delivery element is a catheter.

13. An adjustable anchor for a therapy delivery element, comprising:

a therapy grip element configured to be actuated to at least one of an open position or a closed position, the therapy grip element comprising a first portion and a second portion and having a length defined by the boundaries of a first and second opening, wherein in the open position the grip element comprises a discontinuous inner surface extending the length of the grip element and the first portion is separated from the second portion by a first distance, and wherein in the closed position the first portion is separated from the second portion by a second distance less than the first distance and the inner surface is configured to grippingly engage the therapy delivery element, at least two extension elements connected to the therapy grip element, the extension element configured to extend substantially perpendicular from a therapy delivery element and the extension elements being configured to actuate the therapy grip element; and, a tissue fixation element connected to the extension elements, the tissue fixation element configured to be fixed to a tissue location from an axial direction to the therapy delivery element.

14. The implantable therapy delivery system as in claim 13 wherein the tissue location is near where the therapy delivery element enters the human body on subcutaneous tissue.

15. The implantable therapy delivery system as in claim 13 wherein the two extension elements are actuated with a single pincer motion.

16. The implantable therapy delivery system as in claim 13 wherein the therapy grip element has a substantially rigid grip surface.

17. The implantable therapy delivery system as in claim 13 wherein the therapy grip element is configured in a normally closed position.

18. The implantable therapy delivery element as in claim 13 wherein the therapy grip element covers at least about 25 degrees of the therapy delivery element.

19. The implantable therapy delivery element as in claim 13 wherein the therapy grip element covers at least about 270 degrees of the therapy delivery element.

20. The implantable therapy delivery element as in claim 13 wherein the therapy grip element covers more than about 360 degrees of the therapy delivery element.

21. The implantable therapy delivery element as in claim 13 wherein the therapy grip element has at least two friction pads that engage the therapy delivery element at substantially opposing angles.

22. The implantable therapy delivery element as in claim 21 further comprising release tabs to unlock the therapy grip element before the therapy grip element is actuated from the a closed position to an open position.

23. The implantable therapy delivery element as in claim 13 wherein the therapy grip element further comprises a biasing element.

24. The implantable therapy delivery element as in claim 13 wherein the therapy grip element has a grip stop surface that engages a complimentary extension stop surface to prevent the extension element from actuating the therapy grip element beyond a desired actuation limit.

25. The implantable therapy delivery element as in claim 13 wherein the extension element is positioned at less than about 180 degrees in relation to the therapy delivery element.

26. The implantable therapy delivery element as in claim 13 wherein the extension element is positioned at about 180 degrees in relation to the therapy delivery element.

27. The implantable therapy delivery element as in claim 13 wherein the tissue fixation element has a fixation configuration selected from the group consisting of a suture, a staple, and a screw.

28. The implantable therapy delivery element as in claim 13 wherein the tissue fixation element is configured at a predetermined position in relation to the extension element.

29. The implantable therapy delivery element as in claim 13 wherein the therapy delivery element has at least one anchor position reference.

30. The implantable therapy delivery element as in claim 29 wherein the anchor position reference is selected from the group consisting of a visual reference, a tactile reference, an indentation, and a protrusion.

31. An implantable therapy delivery system having an adjustable anchor, comprising:
   an implantable therapy delivery device;
   at least one therapy delivery element coupled to the implantable therapy delivery device;
   an adjustable anchor coupleable to the therapy delivery element, the adjustable anchor being implantable and including,
      a therapy grip element configured to be actuated to at least one of an open position or a closed position, the therapy grip element comprising a first portion and a second portion and having a length defined by the boundaries of a first and second opening, wherein in the open position the grip element comprises a discontinuous inner surface extending the length of the grip element and the first portion is separated from the second portion by a first distance, and wherein in the closed position the first portion is separated from the second portion by a second distance less than the first distance and the inner surface is configured to grippingly engage the therapy delivery element,
      at least two extension elements connected to the therapy grip element, the extension element extending substantially perpendicular from the therapy delivery element, and the extension elements being configured to actuate the therapy grip element; and,
      a tissue fixation element connected to the extension elements, the tissue fixation element configured to be fixed to a tissue location from an axial direction to the therapy delivery element.

32. The implantable therapy delivery system as in claim 1 wherein the tissue location is near where the therapy delivery element enters the human body on subcutaneous tissue.

33. The implantable therapy delivery system as in claim 1 wherein the two extension elements are actuated with a single pincer motion.

34. The implantable therapy delivery system as in claim 1 wherein the therapy delivery element is an electrical lead.

35. The implantable therapy delivery system as in claim 1 wherein the therapy delivery element is a catheter.

36. The implantable therapy delivery system as in claim 1 wherein the implantable therapy delivery device is a neurostimulator.

37. The implantable therapy delivery system as in claim 1 wherein the implantable therapy delivery device is a therapeutic substance delivery device.

38. The implantable therapy delivery system as in claim 1 wherein the therapy delivery system performs the therapy of sacral nerve stimulation therapy.

39. The implantable therapy delivery system as in claim 1 wherein the therapy delivery system performs the therapy of peripheral nerve stimulation.

* * * * *